United States Patent [19]

Kroener et al.

[11] Patent Number: 4,596,889

[45] Date of Patent: Jun. 24, 1986

[54] PREPARATION OF ALKENYL-LACTIC ACID ESTERS AND THE NOVEL ESTERS OBTAINED

[75] Inventors: Michael Kroener, Mannheim; Walter Goetze, Dannstadt-Schauernheim, both of Fed. Rep. of Germany

[73] Assignee: BASF Aktiengesellschaft, Fed. Rep. of Germany

[21] Appl. No.: 704,152

[22] Filed: Feb. 22, 1985

Related U.S. Application Data

[63] Continuation of Ser. No. 327,701, Dec. 1, 1981, abandoned, which is a continuation of Ser. No. 097,237, Nov. 26, 1979, abandoned.

[30] Foreign Application Priority Data

Dec. 4, 1978 [DE] Fed. Rep. of Germany ....... 2852343

[51] Int. Cl.$^4$ .............................................. C07C 67/22
[52] U.S. Cl. .................................... 560/183; 560/215; 558/6

[58] Field of Search ............................... 560/183, 215; 260/453.7

[56] References Cited

U.S. PATENT DOCUMENTS 2,188,340 12/1939 Dykstra ............................... 564/129

OTHER PUBLICATIONS

Pinner, A. *Die Iminoether und ihre Derivate*, Oppenheimer, Publ. Berlin (1892) pp. 2 and 3.
Edwards, J. D. Jr. J. Heterocyclic Chem. (1967) pp. 487–488.

*Primary Examiner*—Natalie Trousof
*Assistant Examiner*—L. Hendriksen
*Attorney, Agent, or Firm*—Keil & Weinkauf

[57] ABSTRACT

A process for the preparation of an alkenyl-lactic acid ester by reaction of a cyanohydrin with an alcohol in the presence of hydrogen chloride, followed by hydrolysis. The compounds obtained may be used for the preparation of alkaloids and crop protection agents, and as monomers for copolymerization.

5 Claims, No Drawings

PREPARATION OF ALKENYL-LACTIC ACID ESTERS AND THE NOVEL ESTERS OBTAINED

This application is a continuation of application Ser. No. 327,701, filed on Dec. 1, 1981 which is a continuation of Ser. No. 097,237 filed Nov. 26, 1979, both now abandoned.

The present invention relates to a process for the preparation of alkenyl-lactic acid esters, and to novel alkenyl-lactic acid esters.

The reaction of a cyanohydrin with an alcohol and hydrogen chloride to give an imino-ester hydrochloride, from which the corresponding α-hydroxycarboxylic acid ester is then obtained by hydrolysis, has been disclosed. This reaction, introduced by A. Pinner (Die Iminoäther und ihre Derivate", Verlag Oppenheiner, Berlin 1892) can be carried out with very many aliphatic and aromatic nitriles. However, C≡C-unsaturated nitriles, eg. alkenyl cyanides (A. Pinner, Chem. Ber. 17 (1884), 2,007), more or less readily undergo addition of hydrogen chloride to the C≡C-double bond during this reaction, leading to substantial reductions in yield.

The preparation of methyl vinyl-lactate is described in the literature (J. Chem. Soc. 1956, 3,239). It entails a very involved method, namely: the cyanohydrin of methyl vinyl ketone and hydrocyanic acid is first treated with concentrated hydrochloric acid at 90° C. and the resulting water-soluble vinyl-lactic acid is extracted with ether and reacted with diazomethane to give the methyl ester. The yield is 55%.

According to German Laid-Open Application DOS No. 2,711,381, butyl vinyl-lactate is obtained by reacting vinyl-lactic acid with butanol in the presence of hydrochloric acid.

Finally, J. Heteroc. Chem. 1967, 488, describes the preparation of methyl isopropenyl-lactate (methyl 2,3-dimethyl-2-hydroxy-3-butenoate) by reacting the corresponding cyanohydrin with methanol/HCl in ether and then hydrolyzing the ortho-ester. The total yield of this reaction is about 40%.

The present invention relates to a process for the preparation of alkenyl-lactic acid esters of the general formula I

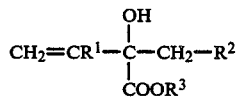

where $R^1$ is hydrogen, methyl or ethyl, $R^2$ is hydrogen or alkyl of 1 to 3 carbon atoms and $R^3$ is alkyl of 1 to 6 carbon atoms, wherein a cyanohydrin of the general formula II

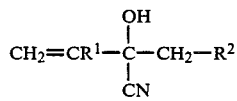

where $R^1$ and $R^2$ have the same meanings as above, is reacted with an alcohol of the general formula III

   III where $R^3$ has the same meaning as above, in the presence of hydrogen chloride, and the resulting reaction mixture is then hydrolyzed.

The present invention further relates to compounds of the general formula V

where $R^4$ is hydrogen, methyl or ethyl, $R^5$ is hydrogen or alkyl of 1 to 3 carbon atoms and $R^6$ is alkyl of 1 to 6 carbon atoms, but $R^4$ and $R^5$ must not both be hydrogen and $R^4$ and $R^6$ must not both be methyl if $R^5$ is hydrogen.

The reaction of II and III with hydrogen chloride results in an imino-ester hydrochloride which can be further converted without first being isolated.

The addition reaction of III with II takes place at from −30° to +50° C., preferably from −10° to +30° C. Stoichiometric amounts of alcohol can be used, but in order to maintain a stirrable consistency of the reaction mixture it is advisable to use an excess of up to 10 moles, preferably from 1.1 to 3 moles, of alcohol per mole of cyanohydrin. The reaction as a rule takes place without the addition of more solvent. However, other inert solvents do not interfere with the reaction. Hydrogen chloride gas, or liquid hydrogen chloride, is introduced into the reaction mixture in stoichiometric amount, or until the reaction mixture is saturated. Advantageously, the hydrogen chloride is employed in an excess of from 1.1 to 3 moles per mole of cyanohydrin.

The cyanohydrin used for the first reaction stage need not be completely anhydrous, nor need be purified by distillation. The simplest and most reliable method is to react an industrially easily obtainable equilibrium mixture (1), having a low content of hydrocyanic acid, with hydrogen chloride in the manner referred to above (cf. German Laid-Open Application DOS No. 2,655,715):

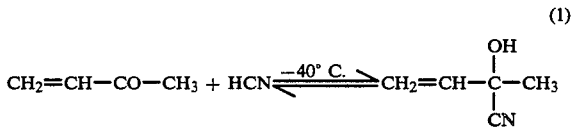

In this reaction, the highly toxic starting materials resulting from equilibration are at the same time rendered harmless.

The imidates formed in the first reaction step are advantageously directly processed further. The excess hydrogen chloride can be stripped off or neutralized. The hydrolysis is in general carried out at pH 1-6, preferably pH 2-4, at from +10° to +70° C., preferably from +20° to +50° C. If an aqueous base is used for the hydrolysis, the latter takes place simultaneously with neutralization. In addition to an aqueous phase, containing ammonium chloride, with or without another salt, e.g. sodium chloride, an organic phase is obtained, which can be washed and worked up by distillation. If approximately stoichiometric amounts of water are used, the ammonium chloride is obtained in a solid form and can be filtered off.

The novel process has the following advantages:

1. Industrially easily accessible, and easily handled, cyanohydrin equilibrium mixtures can be used as the starting materials.

2. The process does not proceed via a free alkenyl-lactic acid, which is very troublesome to isolate and must subsequently be esterified.

3. As a rule, it is not necessary to add an inert solvent. Only in the case of the methyl esters is it advisable to re-extract the aqueous phase with a water-immiscible solvent, eg. an ether, in order to increase the yield, if the product is being worked up from aqueous solution.

4. The process can be carried out as a one-vessel process, causes very little environmental pollution, gives few by-products and presents only a slight safety hazard.

5. The process can be carried out completely continuously. The high heat of solution of hydrogen chloride is alcohols (if gaseous HCl is employed), the high exothermicity of the imidate formation, the hydrolysis of the imidates and, where relevant, the neutralization of excess hydrogen chloride, can be controlled efficiently.

The course of the novel reaction is surprising inasmuch as it was not to be expected that the reaction would take place virtually without such side-reactions as, for example, addition of HCl to the C=C-double bond. Further, it was also unforeseeable that the reaction would give virtually no acid amides. As a consequence, the yield from the reaction is very high.

The compounds prepared according to the invention may be used to prepare alkaloids (J. Heteroc. Chem. 1967, 487) and crop protection agents (eg. Vinclozolin, cf. German Laid-Open Application DOS No. 2,207,576, Example 1), and as monomers for copolymerization (German Laid-Open Application DOS No. 1,795,312).

The Examples which follow illustrate the invention. Parts are by weight.

EXAMPLE 1

48.5 parts of 97% pure vinyl-lactonitrile are added to a solution of 17.7 parts of hydrogen chloride in 17.6 parts of methanol at 0° C. After about 2 hours, spontaneous crystallization occurs and the temperature rises to +10° C. The mixture is left to stand for 12 hours at +5° C. and is then hydrolyzed with 80 parts of water at room temperature. The clear solution which first forms separates, after a short time, into 2 phases. The organic phase is separated off, the aqueous phase is extracted with ether, and the combined organic phases are dried and distilled. 56.7 parts of methyl vinyllactate (90% of theory) are obtained. The purity, according to gas chromatography, is 99.7%; $n_D^{20}$: 1.4325; boiling point: 59° C./20 mm Hg.

EXAMPLE 2

48.5 parts of 97% pure vinyl-lactonitrile are added to a solution of 18 parts of hydrogen chloride in 37 parts of n-BuOH at 0° C. After about 1½ hours, the reaction mixture crystallizes completely. It is then left to stand for 24 hours at +5° C., after which it is hydrolyzed with 80 parts of water at room temperature. The clear solution which is first formed turns cloudy after a short time. After 1½ hours, the organic phase is separated off, washed and distilled. 80.2 parts of n-butyl vinyl-lactate (96% of theory), of boiling point 72°–73° C./11 mm Hg, are obtained.

EXAMPLE 3

56 parts of 99% pure anhydrous hydrocyanic acid, 140 parts of 98% pure methyl vinyl ketone and 2 parts of triethylamine are added simultaneously, in the course of about 1 hour, to 253 parts of isobutanol at −15° C. The reaction mixture is then kept at −40° C. for 2 hours. According to analytical determination of the unconverted hydrocyanic acid, the conversion to cyanohydrin is 90.0%. 121 parts of hydrogen chloride gas are then introduced, during which the temperature rises to 0° C.; the mixture is then left to react for 11 hours, during which the temperature rises to +15° C. In the course thereof, the initially clear reaction solution slowly changes to a suspension. 520 parts of 10% strength sodium hydroxide solution are added in the course of 1 hour, whilst stirring; this raises the pH to 3. The mixture is kept at below 20° C. during the addition, by cooling. The reaction is allowed to continue for a further hour, at 30° C., and 455 parts of organic phase are then separated off. The crude ester is washed and freed from residue by distillation. 431 parts of distillate are obtained, containing, according to gas chromatography, 68.2% by weight of isobutyl vinyl-lactate, corresponding to a yield of 97.2% of theory, based on vinyl-lactonitrile in the equilibrium mixture. Fractional distillation gives 288 parts of pure ester (95% of theory); boiling point: 77° C./13 mm Hg; $n_D^{20}$: 1.4274.

EXAMPLE 4

Using the procedure described in Example 3, 70 parts of hydrocyanic acid are reacted with 174 parts in 96.8% pure methyl vinyl ketone in 271 parts of isobutanol in the presence of 2.7 parts of triethylamine and 166 parts of hydrogen chloride are passed into the cyanohydrin equilibrium mixture, the temperature being initially controlled as described above, though the imidate suspension is subsequently allowed to react for 2 hours at 40° C. After conventional working up, 479 g of primary distillate are obtained, containing 73.4% by weight of isobutyl vinyl-lactate, corresponding to a yield of 94.4% of theory, based on vinyl-lactonitrile in the equilibrium mixture.

EXAMPLE 5

Following a similar procedure to Example 3, 45 parts of hydrocyanic acid are reacted with 105 parts of 99% pure methyl vinyl ketone in 166 parts of isopropanol in the presence of 1 part of triethylamine (cyanohydrin conversion, at −40° C., equal to 92.6% of theory) and 100 parts of hydrogen chloride gas are passed into the reaction mixture. The temperature is then allowed to rise to +15° C. in the course of 32 minutes, after which the mixture is worked up in the conventional manner. 280 parts of primary distillate, containing 70.5% of isopropyl vinyl-lactate, are obtained, corresponding to a yield of 90.1% of theory, based on vinyl-lactonitrile in the equilibrium mixture. Pure ester: boiling point 92° C./70 mm Hg; $n_D^{20}$: 1.4200.

EXAMPLE 6

Following a similar procedure to Example 3, 46 g of 99% pure hydrocyanic acid are reacted with 120 parts of 88.6% pure methyl vinyl ketone (an azeotrope with water) in 191 parts of n-propanol in the presence of 1 part of triethylamine (cyanohydrin conversion, at −40° C., equal to 93% of theory), and 110 parts of hydrogen chloride are passed into the reaction mixture. The temperature is then allowed to rise to +10° C. in the course of 15 hours and the mixture is worked up in the conventional manner. 305 parts of primary distillate are obtained, containing 64.9% by weight of n-propyl vinyl-lactate, corresponding to a yield of 88.8%, based on vinyl-lactonitrile in the equilibrium mixture. Pure ester: boiling point 64° C./10 mm Hg; $n_D^{20}$: 1.4291.

EXAMPLE 7

Following a similar procedure to Example 3, 106 parts of 99% pure hydrocyanic acid are reacted with 263 parts of 99% pure methyl vinyl ketone in 256 parts of absolute ethanol in the presence of 3.4 parts of triethylamine (cyanohydrin conversion, at −40° C., equal to 93%) and 215 parts of hydrogen chloride gas are passed into the reaction mixture. The temperature is then allowed to rise to 20° C. in the course of 10 hours and the mixture is worked up in the conventional manner. Additionally, the aqueous phase is re-extracted with ether. Fractional distillation of the combined organic phases gives 477 g of pure ethyl vinyl-lactate. Yield 89.8% of theory, based on vinyl-lactonitrile in the equilibrium mixture. Without re-extraction of the aqueous phase, the yield is 84.3%. Pure ester: boiling point 74° C./30 mm Hg; $n_D^{20}$: 1.4268.

EXAMPLE 8

Following a similar procedure to Example 3, 70 parts of 98.7% pure hydrocyanic acid are reacted with 216 parts of 89% pure methyl isopropenyl ketone in 205 parts of absolute ethanol in the presence of 2 parts of triethylamine (cyanohydrin conversion, at −40° C., equal to 88 mole %) and 176 parts of hydrogen chloride are passed into the reaction mixture. The reaction is allowed to continue for 48 hours at room temperature, the mixture is then hydrolyzed with 695 parts of 11.8% strength sodium hydroxide solution, and after 5 hours the two-phase mixture is separated. 451 g of organic phase are obtained; this phase gives 370 g of primary distillate. The content of ethyl isopropenyl-lactate is 73.7%, corresponding to a yield of 86.4%, based on the isopropenyl-lactonitrile in the equilibrium mixture. After fractionation, the ester obtained is 97.5% pure: $n_D^{20}$: 1.4360; boiling point 72°-73° C./15 mm Hg.

EXAMPLE 9

Per hour, 49 parts of 98.7% pure hydrocyanic acid, 117 parts of 98% pure methyl vinyl ketone, 212 parts of isobutanol and 1.6 parts of triethylamine are introduced, at −15° C., into the first kettle of a multi-stage cascade. The cyanohydrin conversion rises to 90 mole % in 2 downstream reaction vessels at −40° C. In the 4th reactor, 110 parts per hour of hydrogen chloride are introduced, at 0° C., whilst in the 2 subsequent reactors the reaction is allowed to go to completion at +15° C. In the 6th reactor, about 572 parts per hour of 9% strength aqueous sodium hydroxide solution are added, at +35° C., at a speed such that a pH of 3.0 can be maintained. In the subsequent separating vessel, the organic phase is separated from the aqueous phase. Per hour, 381 parts of organic phase are obtained; after removing the residue by distillation, the yield is 365 g of 67% pure isobutyl vinyl-lactate, corresponding to 96.3% of theory, based on the vinyl-lactonitrile in the cyanohydrin equilibrium mixture in the kettle 3.

EXAMPLE 10

55 parts of 90% pure vinyl isobutyl ketone cyanohydrin are added to a solution of 22 parts of HCl gas in 28.6 parts of ethanol in the course of 1 hour at 0° C. The mixture is then allowed to react for 2 hours at +10° C. and 15 hours at room temperature, after which it is hydrolyzed with 92.6 g of 11% strength sodium hydroxide solution as described in Example 3, except that the time allowed for completion of the reaction at 30° C. is extended to 2 hours, the two-phase mixture is separated and the organic phase is worked up in the conventional manner. 59.7 g of primary distillate, containing 86.8% of ethyl vinyl-isobutylglycollate, corresponding to a yield of 78.5% of theory, are obtained. Pure ester: boiling point 96°-98° C./20 mm Hg.

We claim:

1. A continuous process for the preparation of an alkenyl lactic acid ester of the formula I

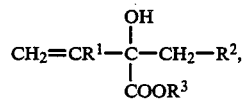

where $R^1$ hydrogen, methyl or ethyl, $R^2$ is hydrogen, or alkyl of 1 to 3 carbon atoms and and $R^3$ is alkyl of 1 to 6 carbon atoms, wherein an essentially water free equilibrium cyanohydrin mixture comprising an alkyl alkenyl ketone of the formula IV

hydrocyanic acid and a cyanohydrin of the formula II

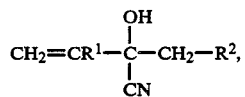

which has been obtained by the reaction of a compound of the formula IV with hydrocyanic acid in an alkanol of the formula III

where $R^3$ has the same meaning as above, is reacted at −30° to 50° C. in the presence of 1.1 to 3 moles of hydrochloric acid based on the cyanohydrin and in the absence of further solvents with the alkanol of the formula

the amount of alkanol being from stoichiometric to 10 moles excess per mole of cyanohydrin, to form a compound of the formula VI

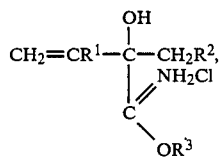

which is then hydrolyzed at a pH from 1 to 6 to the ester of the formula I.

2. A continuous process for preparing compounds of the formula I as described in claim 1, wherein from 1.1 to 3 moles of alkanol is used per mole of cyanohydrin.

3. A continuous process for the preparation of an alkenyl lactic acid ester of the formula I $$CH_2=CR^1-\underset{\underset{COOR^3}{|}}{\overset{\overset{OH}{|}}{C}}-CH_2-R^2, \qquad I$$

where $R^1$ is hydrogen, methyl or ethyl, $R^2$ is hydrogen or alkyl of 1 to 3 carbon atoms and $R^3$ is alkyl of 1 to 6 carbon atoms, wherein an essentially water free equilibrium cyanohydrin mixture comprising an alkyl alkenyl ketone of the formula IV $$CH_2=CR^1-CO-CH_2R^2 \qquad IV,$$

hydrocyanic acid and a cyanohydrin of the formula II $$CH_2=CR^1-\underset{\underset{CN}{|}}{\overset{\overset{OH}{|}}{C}}-CH_2R^2, \qquad II$$

which has been obtained by the reaction of a compound of the formula IV with hydrocyanic acid in an alkanol of the formula III $$R^3OH \qquad III,$$

where $R^3$ has the same meaning as above, is reacted at $-30°$ to $50°$ C. in the presence of 1.1 to 3 moles of hydrochloric acid based on the cyanohydrin and in the absence of further solvents with the alkanol of the formula $$R^3OH \qquad III,$$

the amount of alkanol being from stoichiometric to 10 moles excess per mole of cyanohydrin, to form a compound of the formula VI $$CH_2=CR^1-\underset{\underset{\underset{OR^3}{\diagdown}}{\overset{\diagup NH_2Cl}{C}}}{\overset{\overset{OH}{|}}{C}}-CH_2R^2, \qquad VI$$

which is then hydrolyzed at a pH from 1 to 6 to the ester of the formula I.

4. A continuous process for preparing compounds of the formula I as described in claim 3, wherein from 1.1 to 3 moles of alkanol is used per mole of cyanohydrin.

5. A process as set forth in claim 3, wherein the reaction is carried out in a multi-stage stirred kettle cascade.

* * * * *